United States Patent [19]

Haynes

[11] 4,422,567
[45] Dec. 27, 1983

[54] MEDICAL SUTURING DEVICE

[76] Inventor: Taylor H. Haynes, Medical Plaza Central #1, Salt Lake City, Utah 84112

[21] Appl. No.: 322,351

[22] Filed: Nov. 17, 1981

[51] Int. Cl.$^3$ ............................................. A61B 17/04
[52] U.S. Cl. ................................ 227/19; 128/334 R; 227/DIG. 1; 227/155
[58] Field of Search .................... 227/19, DIG. 1, 152, 227/155; 128/334 R, 335

[56] References Cited

U.S. PATENT DOCUMENTS

| | | | |
|---|---|---|---|
| 3,079,606 | 3/1963 | Bobrev et al. | 227/DIG. 1 |
| 3,252,643 | 5/1966 | Strekopytov et al. | 227/DIG. 1 |
| 3,275,211 | 9/1966 | Hirsch et al. | 227/DIG. 1 |
| 3,494,533 | 2/1970 | Green et al. | 227/DIG. 1 |
| 3,551,987 | 1/1971 | Wilkinson | 227/DIG. 1 |
| 3,643,851 | 2/1972 | Green et al. | 227/DIG. 1 |
| 3,662,939 | 5/1972 | Bryan | 227/DIG. 1 |
| 3,717,294 | 2/1973 | Green | 227/DIG. 1 |
| 3,815,476 | 6/1974 | Green et al. | 227/DIG. 1 |
| 3,819,100 | 6/1974 | Noiles et al. | 227/DIG. 1 |
| 3,822,818 | 7/1974 | Strekopytov et al. | 227/DIG. 1 |
| 3,837,555 | 9/1974 | Green | 227/DIG. 1 |
| 4,166,466 | 9/1979 | Jarvik | 227/DIG. 1 |
| 4,244,372 | 1/1981 | Kapitanov et al. | 227/DIG. 1 |
| 4,354,628 | 10/1982 | Green | 227/DIG. 1 |

OTHER PUBLICATIONS

Exhibit A—Manual distributed by U.S. Surgical Corp. for their TA 30 and TA 55 Stapling Instruments.
Exhibit C—Article entitled "Experimental and Clinical Use of the Soviet Bronchus Stapling Instrument", by Dr. Kavitch, Dr. Brown and Dr. Daviglus–"Surgery", vol. 46 (1959) pp. 97-107.
Exhibit B—Article entitled "Aseptic Technic of Stomach Resections", by Dr. Alador DePetz.
Exhibit D—Article entitled "Closure of Duodenal, Gastric and Intestinal Stumps with Wire Staples: Experimental and Clinical Studies", by Drs. Ravitch, Lane, Cornell, Rivarola and McEnany—Annals of Surgery, vol. 163, No. 4 (Apr. 1966) pp. 573-579.
Exhibit E—Literature Review comprised of articles describing the applications and experience with the prior art.

*Primary Examiner*—Paul A. Bell
*Attorney, Agent, or Firm*—Darle M. Short

[57] ABSTRACT

A medical suturing device is provided which basicly includes a base, a bridge and a head. The bridge extends between and is attached at its ends to the base and the head. The head receives the staples therein (in a staple cartridge) and includes the mechanism to fire the staples. The base includes an anvil which the ends of the staples contact when they are driven through a workpiece. The staple driving mechanism includes an H-shaped body member which receives the cartridge of staples in the lower half of the "H", a rod-like wedge which is slidably received in the upper half of the "H", a rocker plate which is attached perpendicularly to the body member, a rocker arm which is rotatably attached to the rocker plate and interfaces a portion of the wedge, a staple driver which extends between and interfaces the wedge and the staples, and a pneumatic rod which extends from a pneumatic inlet and interfaces the rocker arm. The pneumatic rod is slidable between an in and an extended position. When a pneumatic cylinder is attached to the bolt, and when the pneumatic cylinder is activated, the pneumatic rod slides from the in to the extended position, rotating the rocker arm with respect to the rocker plate, which in turn slides the wedge within the body member driving the staple driver and thus the staples downward through the workpiece.

13 Claims, 10 Drawing Figures

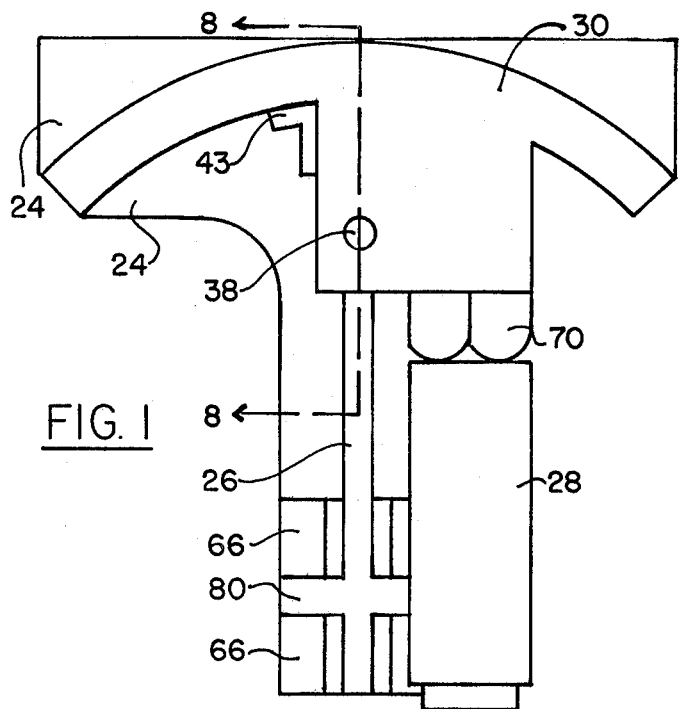
FIG. 1
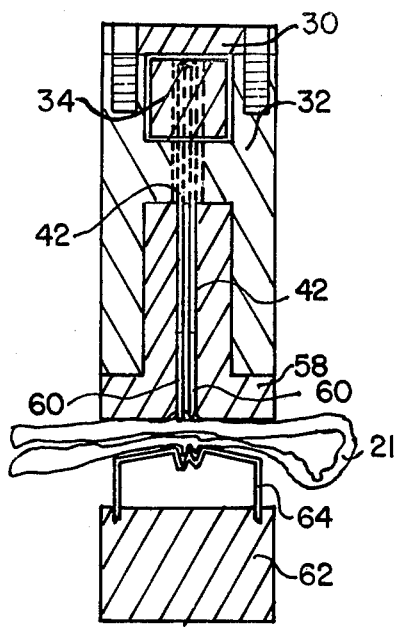
FIG. 5
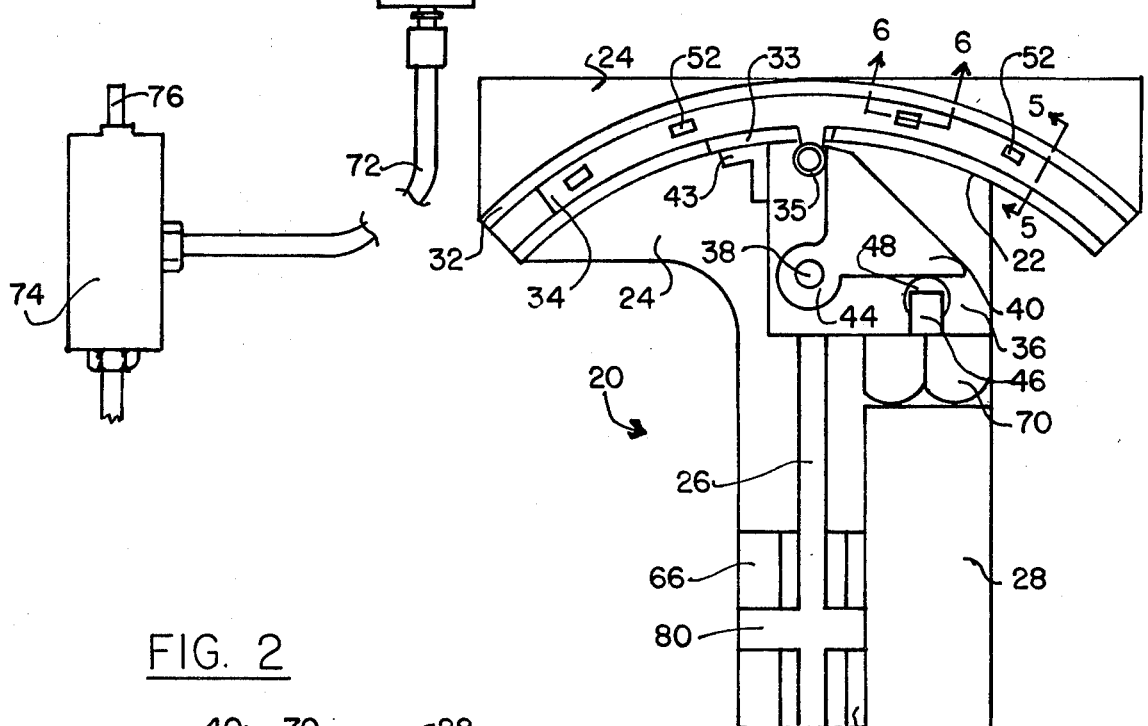
FIG. 2
FIG. 3

MEDICAL SUTURING DEVICE

This invention relates to medical instruments. More particularly, this invention relates to stapling devices for medical suturing.

BACKGROUND OF THE INVENTION

Stapling devices have been used for many years in medicine to suture incisions in various human organs and tissues and to aid in performing resections. In fact, the first such useful device was developed in 1924 by Dr. Aladar DePetz of Hungary.

Since that time, after a brief period of inventive inactivity from 1924 to the 1950's, many different stapling devices have been developed. However not all of these stapling devices can be employed in all medical situations in which a stapling device is helpful. For example, some of the devices will work only on connective tissues, other devices only on hollow organs and lungs, etc. While this invention is not limited for usage on hollow organs and lungs, the usage of this invention in this field will be emphasized.

The medical stapling devices developed over the years, as well as the medical stapling devices currently on the market, for stapling hollow organs and lungs can be classified into two basic types; the straight jaw type and the "C" clamp type. The straight jaw type of stapling device basically comprises a pair of opposing straight jaws wherein one jaw contains the staples and the other jaw functions as the anvil during the stapling process. These stapling devices look much like the jaws of an alligator when the alligator's mouth is open just a crack.

The staplers of this type are powered and operated by a hand mechanism located at and attached to one end of the jaws. The hand mechanism includes a trigger mechanism that is connected by a rod assembly to the jaw containing the staples such that when the trigger mechanism is operated the rod assembly mechanically forces the staples down through the tissue being sutured and against the jaw embodying the anvil.

The "C" clamp type of medical stapler operates in much the same manner as the straight jaw type of stapler but is of a different shape. The "C" clamp type staplers usually have three main portions, a "C" (or "U") shaped head, a trigger mechanism assembly and a long narrow body which connects the head to the trigger mechanism assembly. In these "C" shaped staplers, one of the opposing side walls of the "C" clamp houses the staples while the other opposing side wall functions as the anvil during the stapling process. However, unlike the straight jaw types, the "C" clamp is attached perpendicularly to the narrow body such that the tissue to be stapled is roughly perpendicular to the stapling device when the tissue is properly inserted within the "C" clamp.

All the developments in the medical suturing devices in the last twenty or more years have involved modifications of these two basic stapler types. However, these prior art devices have many shortcomings which greatly effect their efficiency and effectiveness. For example, since the stapling devices are manually fired by squeezing a trigger-like mechanism, the unit is cumbersome to use and the user's hands and arms may obscure the vision of the user during the firing of the devices.

Also, these devices may be easily misfired during the assembly and placement of the devices, causing time delays and possible serious injury to the patient. sometimes, the entire line of staples must be excised if the device misfired before the device was properly positioned.

Furthermore, these devices all have fixed heads attached to relatively long bodies and bulky firing mechanisms. These devices are rather cumbersome to use and impose a severe handicap when working in tight spaces. The positioning of the instrument may take many minutes and much patience on behalf of the operator. This, of course, greatly affects the efficiency and possibly the effectiveness of the surgeon's work.

Some of the prior art instruments involve a complicated procedure comprised of many steps to properly position and set up the devices and fire the devices, taking up valuable time that the medical personnel could use for other tasks.

Also, many of these prior art devices have the disadvantage that the stapling device must be reloaded by putting new staples individually into the proper holes. Since these prior art devices are unitary mechanisms, if a series of sutures is being made on one patient, once the device has been fired the surgeon must wait for the stapling device to be reloaded before proceeding with the suturing.

As can be seen from the above, there exists a need in the art for a stapling device which is safe and efficient to use, which can not be misfired during the assembly or positioning of the device and which can be easily and quickly positioned within the cavity being operated on.

It is the purpose of this invention to fulfill the above needs, plus other needs which will become apparent to those skilled in the art once given the following disclosure:

SUMMARY OF THE INVENTION

Generally speaking this invention provides a medical suturing device comprising a base, a head removably attached to said base, said base having a portion opposite said head, said head including a body member, a rocker plate, a rocker arm rotatably attached to said rocker plate and a wedge, said rocker plate being attached to said body member, said body member including a first means to receive staples and a second means to receive said wedge such that said wedge is slidably located in said second means, said wedge having a portion which abuts the rocker arm, said head also including a third means to attach to a power mechanism, said third means including a member which abuts said rocker arm and has an in and an extended position, and a staple driver which extends between said wedge and said staples, wherein when said power mechanism is activated, said member moves from the in to the extended position, rotating said rocker arm which in turn slides said wedge within said first means and drives said staples through a workpiece.

In some embodiments of this invention, the device includes a bridge which extends between and is attached to the head and the base. The base may have attached thereto a staple anvil which interfaces the staples and bends the ends of the staples under and towards each other when the staples are driven through the workpiece. The bridge is attached to the head and the base in a manner such that the bridge can be easily and quickly detached from either the head or the base or both. This enables the suturing device to be quickly assembled and disassembled as well as allowing for a quick change of heads if the surgeon employing the device decides that another shape or size head is needed, or if the surgeon is doing a series of stapling operations that require different heads.

In other embodiments of this invention, the device is designed and constructed such that it is attachable to a pneumatic cylinder which is the power mechanism for the device. In these embodiments the member may be a pneumatic rod which extends outwardly from the pneumatic cylinder and slides from said in to said extended positions whenever said pneumatic cylinder is activated.

The body member may have an H-shaped cross section wherein the first means comprises the bottom half of the H-shaped body member and the second means comprises the top half of the H-shaped body member. The wedge can then be a rod-like member designed to slide within the top half of the body member. Moreover, the wedge may include a knob-like portion that extends inwardly from said wedge and abuts the rocker arm.

In certain embodiments of this invention the staples and staple driver may be embedded in a cartridge which snaps on the bottom half of the body member.

This invention has many advantages over the prior art. One of these advantages is that the devices according to this invention can be designed such that it is impossible to misfire the devices during the assembly or positioning of the devices. The power source for some embodiments of the subject invention is a pneumatic cylinder. These embodiments are designed such that the pneumatic cylinder does not need to be attached to the head of the device until the device is completely assembled and properly positioned, such that the device can not even be fired until it is properly assembled. This feature is not limited to embodiments employing pneumatic power but can be built into other embodiments of the invention which do not employ pneumatic cylinders as the power source.

Another advantage of this invention is the compactness with which the subject devices can be built. This feature enables the subject devices to be more quickly and easily positioned for firing. In some circumstances, the entire device may fit within the cavity being worked on.

Yet another advantage of devices according to this invention is that a plurality of shapes and sizes of heads can be employed with any one device. This enables the subject devices to be effectively used in a wide variety of situations and at odd angles and in tight spaces. The prior art devices do not have this capability. The present invention is capable of being used with precision in tight spaces.

A further advantage of this invention is that in some embodiments the device is pneumatically powered and may be designed to be activated by a foot pedal instead of being hand operated. This is one of the features of this invention which enables these devices to be used in tight places since one of the surgeon's hands does not need to be on the device to fire the device. Furthermore, since the surgeon's hands do not need to be on the handle to fire the device, the line of vision between the surgeon and the stapler is not blocked by his hands. This feature also leads to a more accurate shooting of the stapling device since the surgeon's hands do not have to move to operate the device.

It is also an advantage of this invention that by choosing which head to use, the surgeon also determines the positioning and spacing of the stapling arm with respect to the anvil.

Another advantage of this invention is that, since the heads are interchangable, the surgeon can quickly change the shape or size of stuture he wants to make without any logistic delay. The second head can be quickly attached to the device even if the first head has already been attached to the device, before the surgeon is ready for it. This feature is also important if the surgeon is making a series of sutures, each requiring a different head.

A further advantage of some embodiments of this invention is that, since pneumatic power is used, the power applied is consistent, smooth and a sufficient quantity is available.

It is also an advantage of this invention that the mechanism for converting force on the pneumatic rod to the staples is relatively simple mechanically and compact. This feature makes the present devices more dependable, easier to use and contributes to the compactness to the present devices.

The invention will now be described herein with respect to the drawings wherein:

IN THE DRAWINGS

FIG. 1 is a top view of one embodiment of this invention.

FIG. 2 is a side view of the embodiment of this invention illustrated in FIG. 1.

FIG. 3 is a top view of the embodiment of this invention illustrated in FIGS. 1 and 2 with the top plate removed and the pneumatic rod in the in position.

FIG. 5 is a partial cross sectional view taken along line 5—5 of FIG. 3 (with the top plate added).

DETAILED DESCRIPTION OF THE DRAWINGS

Figure 4:
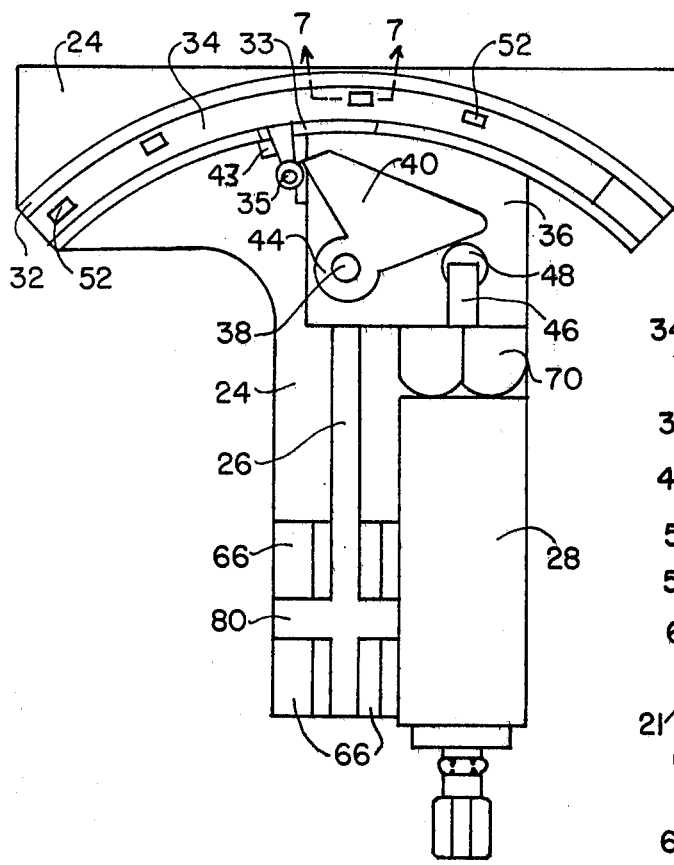
FIG. 4 is a top view of the embodiment of this invention illustrated in FIGS. 1-3 with the top plate removed and the pneumatic rod in the extended position.

Referring to the Figures, suturing device 20 is for stapling workpieces, such as workpiece 21, and includes basicly head 22, base 24 and bridge 26. This embodiment of the invention is designed to be readily attachable to a power source such as pneumatic cylinder 28. Head 22 is connected to base 24 by bridge 26 which is easily detachable from both head 22 and base 24, as will be discussed below. Head 22 is easily detachable from base 24 so that a plurality of heads of different shapes and sizes can be interchanged with base 24 and bridge 26.

Head 22 includes top plate 30, H-shaped body member 32, wedge 34, rocker plate 36, rocker pivot pin 38, rocker arm 40, pneumatic rod 46, slotted brackets 43 and pneumatic bolt 70. Body member 32 has an H-shaped vertical cross section, and in the embodiment of the invention illustrated in the Figures, is in the shape of an arc. Rocker plate 36 and top plate 30 are flat plates which are attached perpendicularly to member 32 and are of the shapes shown in FIGS. 1, 3 and 4. Rocker pivot pin 38 extends between and is attached at its ends to rocker plate 36 and top plate 30.

Rocker arm 40 is a triangular member with a hub 44 which rotatably receives rocker pivot pin 38 therein. Rocker arm 40 lies between rocker plate 36 and top plate 30 in the vertical and is designed to be rotated between the two positions shown in FIGS. 3 and 4, respectively. Rocker arm 40 interfaces with pneumatic rod 46 and wedge 34 described below.

Pneumatic rod 46 extends from pneumatic bolt 70 (which is fixedly attached to top plate 30 and rocker plate 36) between top plate 30 and rocker plate 36 in a slot (not shown) and has wheel 48 attached to the end thereof. In the embodiment of the invention illustrated in the Figures, pneumatic rod 46 has a hexagonal cross section. Pneumatic rod 46 slides back and forth between two positions, an in position as shown in FIG. 3, and an extended position as shown in FIG. 4. Pneumatic rod 46 is powered between these two positions by pneumatic cylinder 28. Wheel 48 has a vertical axis of rotation and abuts rocker arm 40.

Figure 6:
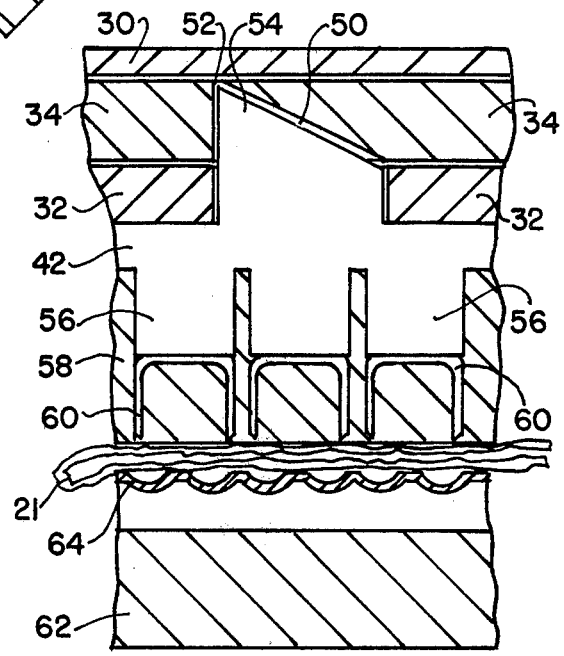
FIG. 6 is a partial cross sectional view taken along line 6—6 of FIG. 3 (with the top plate added).
Figure 7:
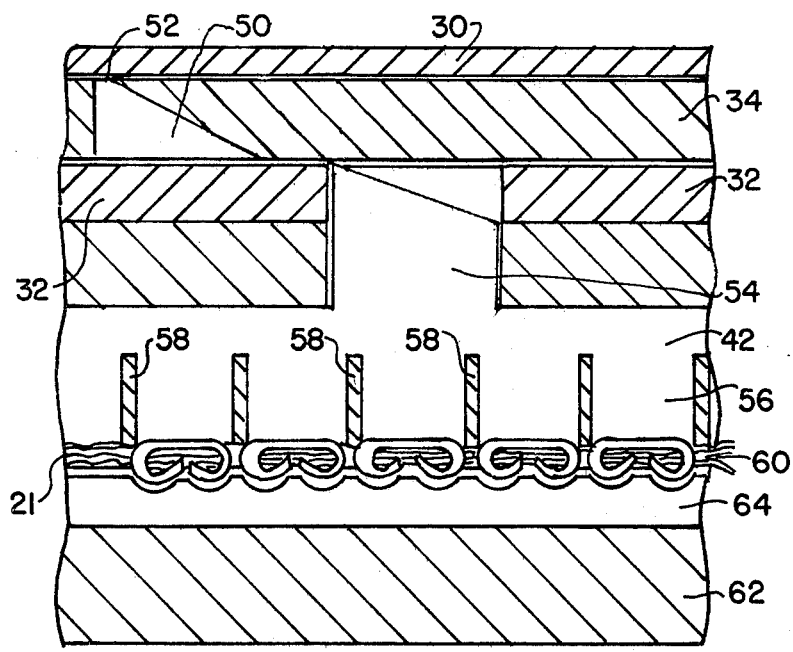
FIG. 7 is a partial cross sectional view taken along line 7—7 of FIG. 4 (with the top plate added).
Figure 8:
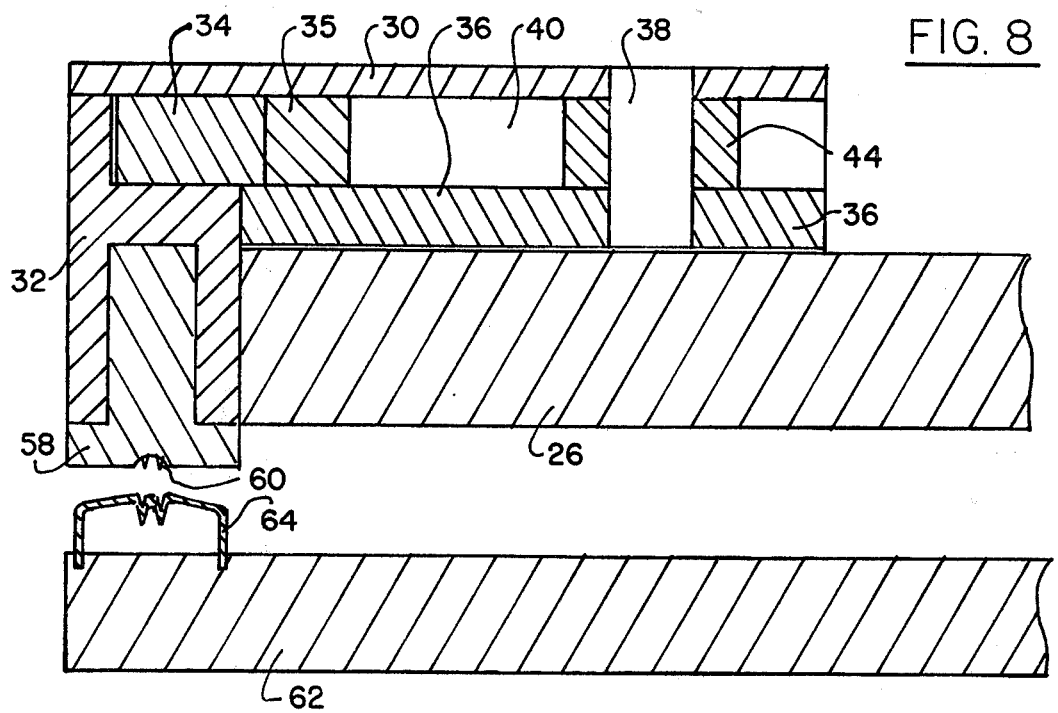
FIG. 8 is a cross sectional view taken along line 8—8 of FIG. 1.

In the embodiment of this invention illustrated in the Figures, wedge 34 is a solid rod-like member shaped in an arc (see FIG. 5). However, spaced within wedge 34 are slots 50 (see FIGS. 6 and 7) which are spaced and positioned to interface with staple drivers 42 (as described below).

Slots 50 are in the shape of a right angle wedge and extend all the way thru wedge 34 such that holes 52 (see FIGS. 3, 4, 6 and 7) are formed in the top of wedge 34. Wedge 34 is, of course, of a size and shape such that it is received in the top slot defined by the two uprights of H-shaped member 34 and is designed to slide back and forth within this top slot. Wedge 34 includes knob 35 which extends inward from body member 32 and abuts rocker arm 40. Note that slot 33 has been cut away from the inner upright of body member 32 so that knob 35 is free to swing in a short arc with respect to body member 32.

Figure 9:
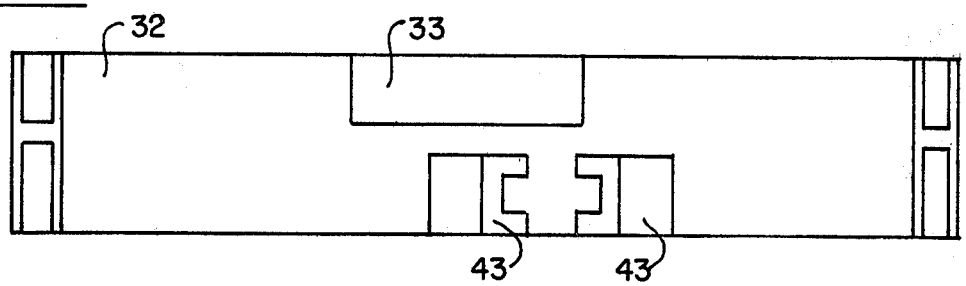
FIG. 9 is a rear view of the head of the embodiment of this invention illustrated in FIGS. 1-8.

Slotted brackets 43 are two opposing slotted back angle bars spaced apart and are attached to the inside of H-shaped member 32 under rocker plate 36 (see FIG. 9). Slotted brackets 43 act as the front point of attachment of bridge 26 to head 22.

This embodiment of the invention is designed to be employed with a staple cartridge, such as staple cartridge 58, which can be snapped onto the lower portion of body member 32. Staple cartridge 58 can be of a plastic material and have embedded therein staples 60 and staple drivers 42.

Staple drivers 42 are comprised of sheets of metal stamped into the shape of a "U" with the bottom of the "U" projecting upward (as shown in the Figures). In this embodiment of the invention, staple drivers 42, as well as staples 60 are embedded into staple cartridge 58, by a plastic molding process. Staple drivers 42 include engaging portions 54 and portions 56. Engaging portions 54 comprise the top portions of staple drivers 42 and extend upward, when the suturing device is assembled and ready for firing, through slots in the cross bar of bottom member 32 into slots 50 in wedge 34 when wedge 34 is in the non-fired position (see FIG. 6). The top slanted edges of engaging portions 54 interface with the sloped surfaces of slot 50. Portions 56 comprise the lower portions of staple drivers 42 and extend downwardly and abut the top of staples 60, i.e., the bottom edges of portions 56 abut the top of staples 60. The staple drivers 42 and staples 60 are held in this relationship by the plastic material in which the same are embedded. The two legs of the staples are in approximately the same plane (i.e. in line) with the two side plates of staple driver 42, so that when staple driver 42 is driven downward (as later discussed), portions 56 of staple driver 42 will push staples 60 out of staple cartridge 58.

Base 24 is comprised of base plate 62, anvil 64 and angle segments 66. Base plate 62 is a flat plate which is designed to extend under head 22 and back from head 22 a set distance to give stability to the unit.

Anvil 64 is attached to the top of base plate 62 and is designed to be directly opposite body member 32 and staple cartridge 58. Anvil 64 has staple indents 68 therein to curve the points of the staples inward and towards each other when suturing device 20 is operated.

The embodiment of base 24 shown in the Figures includes four angle segments 66 which are attached to the top of base plate 62 in the location shown in FIGS. 1-4. Angle segments 66 have one leg attached to base plate 62 such that the other leg stands vertical, perpendicular to base plate 62. Angle segments 66 are spaced in two parallel pairs so that bridge 26 is received by angle segments 66 as described below.

Figure 10:
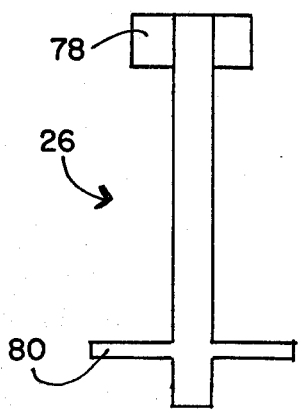
FIG. 10 is a top view of the bridge of the embodiment of this invention illustrated in FIGS. 1-9.

Bridge 26, in the embodiment of this invention shown in the Figures, is a unitary piece of material of a shape and size compatible with angle segments 66 and slotted brackets 43 (see FIG. 10). Bridge 26 comprises a long rectangular portion, which fits vertically between the two pair of angle segments 66 and the two slotted brackets 43, and two pair of flanges, front flanges 78 and rear flanges 80 which interconnect with slotted brackets 43 and angle segments 66, respectively. Front flanges 78 (see FIG. 10) are horizontal and fit into the horizontal slots of slotted brackets 43 (shown in FIG. 9). Rear flanges 80 are vertical and fit between the edges of the adjacent pairs of angle segments 66 (see FIG. 4). In addition, latches (not shown) can be provided to attach bridge 26 to head 22 and base 24.

Pneumatic cylinder 26 is designed such that it readily attaches to and detaches from pneumatic bolt 70. Pneumatic cylinder 28 is controlled by valve assembly 74 which is connected to pneumatic cylinder 28 by pneumatic hose 72. Valve assembly 74 is connected to an inlet air source and when the valve is opened by pushbutton 76, air passes on to pneumatic cylinder 28 to activate suturing device 20. Valve assembly 74 can either be hand-operated or it can be positioned on the floor so that it can be foot-operated.

Suturing device 20 is employed as follows. First the device is assembled by attaching and latching (if latches are provided) bridge 26 to head 22 and base 24. Front flanges 78 are inserted within slotted brackets 43 and rear flanges 80 are placed between angle segments 66. Also during this time, staple cartridge 58 is snapped onto the bottom of body member 32.

Next, workpiece 21 is inserted between anvil 64 and staple cartridge 58. When the surgeon employing this device has workpiece 21 properly positioned to receive the staples 60, pneumatic cylinder 28 (or other power source) is attached to pneumatic bolt 70. By not connecting the power source to the device until this time, any accidental firing of the stapling device during the assembly and positioning of the device is avoided. When the pneumatic cylinder 28 is properly attached, the surgeon activates, or directs another person to activate, suturing device 20 by pushing on pushbutton 76.

When pneumatic cylinder 28 is so activated, the pneumatic force released pushes pneumatic rod 46 and wheel 48 from the retracted (or in) position shown in FIG. 3 to the extended position shown in FIG. 4. This movement in turn causes rocker arm 40 to rotate around rocker pivot pin 38 between its two positions shown in FIGS. 3 and 4. When rocker arm 40 so rotates, it pushes on knob 35 and moves knob 35 and wedge 34 to the left, as viewed from the top of FIGS. 3 and 4.

When wedge 34 moves to the left, it pushes staple driver 42 downward as follows. Wedge 34 has spaced slots 50 therein as described above. When wedge 34 is in the stable condition, shown in FIGS. 3, 5 and 6, engaging portions 54 of staple drivers 42 project upward into these slots 50. As wedge 34 is moved to the left, the sloped surfaces of slots 50 of wedge 34 interface with the sloped surfaces of engaging portions 54 and pushes engaging portion 54 and thus the entire staple driver 42 downward. When staple driver 42 is driven downward, its portions 56 push staples 60 out of the staple cartridge 58 and into workpiece 21. After staples 60 pass thru workpiece 21 staples 60 contact anvil 64 and the ends are bent under themselves in the final stapled position.

After stapling device 20 has been fired, the spent cartridge 58 can be snapped off, after disconnecting pneumatic cylinder 28 from pneumatic bolt 70, and a new cartridge 58 can be snapped on to replace it. Stapling device 20 is then ready to repeat the above operating cycle. If desired, the heads can be changed at this time.

Once given the above disclosure, many other embodiments, modifications and improvements of this invention will become apparent to those skilled in the art. Such other embodiments, modifications and improvements are considered to be within the scope of this invention as defined by the following claims:

I claim:
1. A medical suturing device comprising:
a base,
a head removably attached to said base, said base having a portion opposite said head,
said head including a body member, a rocker plate, a rocker arm rotatably attached to said rocker plate and a wedge,
said rocker plate being attached to said body member, said body member including a first means for receiving staples and a second means for receiving said wedge such that said wedge is slidably located in said second means,
said wedge having a portion which abuts the rocker arm,
said head also including a third means for attaching to a power mechanism,
said third means including a member which abuts said rocker arm and has an in and an extended position, and,
a staple driver which extends between said wedge and said staples,
wherein when said power mechanism is activated, said member moves from the in to the extended position, rotating said rocker arm which in turn slides said wedge within said first means and drives said staples through a workpiece.

2. A medical suturing device according to claim 1 further comprising:
a bridge which extends between and is attached to said head and said base,
wherein said base has an anvil attached thereto which opposes said staples when said device is assembled.

3. A medical suturing device according to claim 2 wherein:
said power mechanism is a pneumatic cylinder,
said third means includes a pneumatic bolt, and
wherein said member is a pneumatic rod which extends inwardly from said pneumatic bolt and slides from said in to said extended position whenever said pneumatic cylinder is activated.

4. A medical suturing device according to claim 3 wherein:
said body member is H-shaped having two vertical members and a cross bar, said first means comprises the bottom portion of said body member and said second means comprises the top portion of said body member.

5. A medical suturing device according to claim 4 wherein:
said wedge is a rod shaped member having a knob extending therefrom towards the rocker arm, said rocker arm abutting said knob.

6. A medical suturing device according to claim 5 wherein:
said staple driver extends through holes in said cross bar of said body member and has an up and a down position,
said wedge having slots therein,
said slots engaging said staple driver and driving said staple driver from the up to the down position when said wedge is slid within said second means.

7. A medical suturing device according to claim 6 wherein said slots are wedge-shaped, and wherein said staple driver has a wedge-shaped portion which fits in said slots.

8. A medical suturing device according to claim 7 wherein said staples and said staple driver are partially embedded in a cartridge which is designed to snap into said first means.

9. A medical suturing device according to claim 8 wherein said base is a flat plate having means for attaching to said bridge.

10. A medical suturing device according to claim 9 wherein said bridge is an elongated member which attaches at one end to said base and at the other end to said head.

11. A medical suturing device according to claim 10 further comprising means for latching said bridge to said head and said base.

12. A medical suturing device according to claim 11 wherein said staple driver is a flat plate bent into a U-shape.

13. A medical suturing device comprising:
a base including a staple anvil,
a head including a rocker plate, a rocker arm, a wedge, a first means for receiving a staple cartridge and said wedge, a second means for engaging a pneumatic cylinder,
said head being connected to said base such that said staple cartridge is opposite said anvil,
said head further including third means for driving staples into a workpiece and a pneumatic rod which is powered by said pneumatic cylinder and has in and extended positions, said pneumatic rod engaging said rocker arm such that when said rod goes from the in to the extended position, said rocker arm rotates,
said rocker arm engaging said wedge such that when said rocker arm is rotated by said pneumatic rod, said wedge is driven into engagement with said third means and said third means drives staples into a workpiece.

* * * * *